US010682040B2

(12) United States Patent
Higuchi et al.

(10) Patent No.: US 10,682,040 B2
(45) Date of Patent: Jun. 16, 2020

(54) ENDOSCOPE APPARATUS AND FOCUS CONTROL METHOD FOR ENDOSCOPE APPARATUS

(71) Applicant: OLYMPUS CORPORATION, Hachioji-shi, Tokyo (JP)

(72) Inventors: Keiji Higuchi, Kunitachi (JP); Koichiro Yoshino, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 527 days.

(21) Appl. No.: 15/342,492

(22) Filed: Nov. 3, 2016

(65) Prior Publication Data

US 2017/0071452 A1    Mar. 16, 2017

Related U.S. Application Data

(63) Continuation of application No. 13/953,519, filed on Jul. 29, 2013, now Pat. No. 9,516,999.

(30) Foreign Application Priority Data

Aug. 2, 2012  (JP) .................................. 2012-171678

(51) Int. Cl.
*A61B 1/00* (2006.01)
*A61B 1/04* (2006.01)
(Continued)

(52) U.S. Cl.
CPC ...... *A61B 1/00096* (2013.01); *A61B 1/00006* (2013.01); *A61B 1/00009* (2013.01);
(Continued)

(58) Field of Classification Search
CPC ... A61B 1/00188; A61B 1/00006; A61B 1/06; G02B 7/34; G02B 7/38; H04N 5/23212; G03B 13/36
(Continued)

(56) References Cited

U.S. PATENT DOCUMENTS 3,946,222 A * 3/1976 Swanberg ................ G02B 7/34
                                                     250/201.4
4,500,189 A * 2/1985 Aoki ........................ G02B 7/34
                                                     250/201.8
(Continued)

FOREIGN PATENT DOCUMENTS

JP      08136832 A    5/1996
JP      10073758 A    3/1998
(Continued)

OTHER PUBLICATIONS

Japanese Office Action (and English translation thereof) dated Jun. 21, 2016, issued in counterpart Japanese Application No. 2012-171678.

*Primary Examiner* — Timothy J Neal
*Assistant Examiner* — Jae Woo
(74) *Attorney, Agent, or Firm* — Holtz, Holtz & Volek PC

(57) ABSTRACT

An endoscope apparatus including an imaging section that includes a phase difference detection element for implementing phase detection autofocus, and acquires a captured image; a phase difference calculation section that calculates a phase difference based on a signal output from the phase difference detection element; a lens position selection section that selects a lens position that is either a near point-side lens position or a far point-side lens position based on the phase difference, the near point-side lens position and the far point-side lens position being discrete lens positions set in advance; a driver section that changes a lens position of the imaging section to the lens position selected by the lens position selection section; and a control section that controls an intensity of illumination light that is applied to an object. The lens position selection section determines whether or not the intensity is smaller than a given threshold value when the phase difference calculation section cannot detect the phase difference, selects the near point-side lens position (Continued)

when the lens position selection section has determined that the intensity is smaller than the threshold value, and selects the far point-side lens position when the lens position selection section has determined that the intensity is larger than the threshold value.

10 Claims, 14 Drawing Sheets

(51) Int. Cl.
 *A61B 1/06* (2006.01)
 *G02B 7/34* (2006.01)
 *G02B 23/24* (2006.01)
 *G02B 7/09* (2006.01)
 *H04N 5/225* (2006.01)

(52) U.S. Cl.
 CPC ............ *A61B 1/00188* (2013.01); *A61B 1/04* (2013.01); *A61B 1/06* (2013.01); *G02B 7/09* (2013.01); *G02B 7/34* (2013.01); *G02B 23/243* (2013.01); *H04N 5/2256* (2013.01); *H04N 2005/2255* (2013.01)

(58) Field of Classification Search
 USPC .................................. 600/167, 168, 117, 118
 See application file for complete search history.

(56) References Cited

U.S. PATENT DOCUMENTS

| | | | | |
|---|---|---|---|---|
| 4,529,287 A * | 7/1985 | Karasaki | G02B 7/34 | 250/201.8 |
| 4,740,678 A * | 4/1988 | Horikawa | G02B 7/34 | 250/201.8 |
| 4,905,032 A * | 2/1990 | Ishida | G02B 7/346 | 396/104 |
| 5,325,146 A * | 6/1994 | Toji | G02B 7/102 | 348/353 |
| 5,386,105 A * | 1/1995 | Quinn | G06K 7/10811 | 235/462.22 |
| 5,532,783 A * | 7/1996 | Kusaka | G02B 7/34 | 396/116 |
| 6,108,495 A * | 8/2000 | Takahata | G02B 7/32 | 396/106 |
| 6,166,784 A | 12/2000 | Murata et al. | | |
| 6,288,767 B1 | 9/2001 | Murata et al. | | |
| 6,473,126 B1 * | 10/2002 | Higashihara | H04N 5/23212 | 348/345 |
| 6,496,225 B1 | 12/2002 | Higashihara | H04N 5/23212 | 348/345 |
| 6,818,875 B1 * | 11/2004 | Suzuki | G02B 7/28 | 250/201.2 |
| 6,829,008 B1 * | 12/2004 | Kondo | G02B 7/34 | 348/302 |
| 2001/0026683 A1 * | 10/2001 | Morimoto | G02B 7/28 | 396/89 |
| 2001/0035910 A1 * | 11/2001 | Yukawa | H04N 5/23212 | 348/349 |
| 2003/0040659 A1 * | 2/2003 | Kazakevich | A61B 1/00188 | 600/167 |
| 2004/0037547 A1 * | 2/2004 | Okawara | G03B 13/34 | 396/133 |
| 2004/0057712 A1 * | 3/2004 | Sato | G03B 3/00 | 396/89 |
| 2004/0257461 A1 * | 12/2004 | Toyomura | G02B 7/102 | 348/345 |
| 2005/0001924 A1 * | 1/2005 | Honda | H04N 5/23212 | 348/348 |
| 2005/0185086 A1 * | 8/2005 | Onozawa | H04N 5/23212 | 348/349 |
| 2006/0120709 A1 * | 6/2006 | Kobayashi | G02B 7/102 | 396/80 |
| 2006/0165402 A1 * | 7/2006 | Ishii | G03B 13/30 | 396/123 |
| 2007/0055104 A1 * | 3/2007 | Kumei | A61B 1/018 | 600/176 |
| 2009/0167930 A1 * | 7/2009 | Safaee-Rad | G02B 7/38 | 348/347 |
| 2009/0185068 A1 * | 7/2009 | Iwasaki | G02B 7/36 | 348/345 |
| 2009/0190023 A1 * | 7/2009 | Mise | G03B 13/00 | 348/345 |
| 2009/0190909 A1 | 7/2009 | Mise et al. | | |
| 2010/0214452 A1 * | 8/2010 | Kawarada | G02B 7/346 | 348/255 |
| 2011/0019028 A1 * | 1/2011 | Kimijima | G02B 7/34 | 348/222.1 |
| 2011/0032411 A1 * | 2/2011 | Hirai | G02B 7/36 | 348/345 |
| 2011/0158627 A1 * | 6/2011 | Hirai | G03B 3/10 | 396/137 |
| 2011/0234768 A1 * | 9/2011 | Pan | G02B 7/38 | 348/47 |
| 2011/0274420 A1 * | 11/2011 | Yasuda | G02B 7/36 | 396/125 |
| 2011/0293256 A1 * | 12/2011 | Ishiwata | G02B 7/38 | 396/104 |
| 2012/0044408 A1 * | 2/2012 | Sasaki | H04N 5/23212 | 348/345 |
| 2012/0105590 A1 * | 5/2012 | Fukumoto | H04N 5/23212 | 348/46 |
| 2012/0154547 A1 * | 6/2012 | Aizawa | G02B 7/285 | 348/47 |
| 2012/0327291 A1 * | 12/2012 | Takeuchi | H04N 5/23212 | 348/353 |
| 2013/0028582 A1 * | 1/2013 | Batur | G03B 13/36 | 396/124 |
| 2013/0162861 A1 * | 6/2013 | Yamamoto | H04N 9/045 | 348/222.1 |
| 2014/0030716 A1 | 1/2014 | Chen et al. | | |
| 2014/0118611 A1 * | 5/2014 | Hamano | H04N 5/23212 | 348/350 |
| 2014/0153085 A1 * | 6/2014 | Dobbie | G02B 7/08 | 359/356 |
| 2014/0210974 A1 * | 7/2014 | Yoshino | G02B 23/2438 | 348/65 |
| 2014/0267869 A1 * | 9/2014 | Sawa | H04N 5/23293 | 348/333.03 |
| 2014/0300716 A1 * | 10/2014 | Tsuruoka | G02B 23/2484 | 348/65 |
| 2014/0307072 A1 * | 10/2014 | Takahashi | H04N 5/23296 | 348/65 |
| 2014/0376779 A1 * | 12/2014 | Kim | G06K 9/348 | 382/106 |
| 2015/0042866 A1 * | 2/2015 | Wakazono | H04N 5/23212 | 348/346 |

FOREIGN PATENT DOCUMENTS

JP 2011139760 A * 7/2011
JP 2011139760 A 7/2011

* cited by examiner

FIG. 3

| PHASE DIFFERENCE (NEAR) | DISTANCE TO OBJECT | PHASE DIFFERENCE (FAR) |
|---|---|---|
| ⋮ | ⋮ | ⋮ |
| pi | di | ⋮ |
| ⋮ | ⋮ | ⋮ |
| 0 | dp0 | ⋮ |
| ⋮ | ⋮ | ⋮ |
| pk | dk | qk |
| ⋮ | ⋮ | ⋮ |
| ⋮ | dq0 | 0 |
| ⋮ | ⋮ | ⋮ |
| ⋮ | dj | qj |
| ⋮ | ⋮ | ⋮ |

FIG. 10

| PHASE DIFFERENCE (NEAR) | DISTANCE TO OBJECT | PHASE DIFFERENCE (FAR) |
|---|---|---|
| ⋮ | ⋮ | ⋮ |
| pi | di | ⋮ |
| ⋮ | ⋮ | ⋮ |
| 0 | dp0 | ⋮ |
| ⋮ | ⋮ | ⋮ |
| ⋮ | dk1 | qk1 |
| ⋮ | ⋮ | ⋮ |
| pk2 | dk2 | ⋮ |
| ⋮ | ⋮ | ⋮ |
| ⋮ | dq0 | 0 |
| ⋮ | ⋮ | ⋮ |
| ⋮ | dj | qj |
| ⋮ | ⋮ | ⋮ |

FIG. 14

| POSITION OF MOVABLE LENS | RATIO OF MOVING AMOUNT OF MOVABLE LENS TO MOVING AMOUNT OF IMAGE POSITION |
|---|---|
| x1 | R1 |
| x2 | R2 |
| x3 | R3 |
| ⋮ | ⋮ |

FIG. 15

| POSITION OF MOVABLE LENS | RATIO OF MOVING AMOUNT OF MOVABLE LENS TO MOVING AMOUNT OF IMAGE POSITION | DISTANCE BETWEEN IMAGE PLANE AND EXIT PUPIL | DISTANCE BETWEEN CENTERS OF GRAVITY OF PUPILS |
|---|---|---|---|
| x1 | R1 | F1 | G1 |
| x2 | R2 | F2 | G2 |
| x3 | R3 | F3 | G3 |
| ⋮ | ⋮ | ⋮ | ⋮ |

ENDOSCOPE APPARATUS AND FOCUS CONTROL METHOD FOR ENDOSCOPE APPARATUS

CROSS-REFERENCE TO RELATED APPLICATIONS

This is a Continuation of U.S. application Ser. No. 13/953,519, filed Jul. 29, 2013, which is based upon and claims the benefit of priority from prior Japanese Patent Application No. 2012-171678, filed Aug. 2, 2012, the entire contents of both of which are incorporated herein by reference.

BACKGROUND

The present invention relates to an endoscope apparatus, a focus control method for an endoscope apparatus, and the like.

When performing screening examination utilizing an endoscope apparatus, the endoscope apparatus is required to achieve as deep a depth of field as possible so that the user can observe a deep digestive tract. In recent years, the number of pixels of the image sensor used for the endoscope apparatus has been increased, and it has become difficult to capture a panfocus (deep-focus) image since the aperture is limited due to the diffraction limit. The user must bring the object into focus when it is difficult to capture a panfocus (deep-focus) image.

For example, JP-A-2011-139760 discloses an endoscope apparatus that divides the captured image into a plurality of areas, selects the autofocus (AF) control target area from the plurality of areas, and performs an autofocus control process based on the image in the selected area. According to the endoscope apparatus disclosed in JP-A-2011-139760, the user need not manually perform a focus control process.

SUMMARY

According to one aspect of the invention, there is provided an endoscope apparatus comprising:

an imaging section that includes a phase difference detection element for implementing phase detection autofocus, and acquires a captured image;

a phase difference calculation section that calculates a phase difference based on a signal output from the phase difference detection element;

a lens position selection section that selects a lens position that is either a near point-side lens position or a far point-side lens position based on the phase difference, the near point-side lens position and the far point-side lens position being discrete lens positions set in advance; and a driver section that changes a lens position of the imaging section to the lens position selected by the lens position selection section.

According to another aspect of the invention, there is provided a focus control method for an endoscope apparatus comprising:

calculating a phase difference based on a signal output from a phase difference detection element for implementing phase detection autofocus that is included in an imaging section;

selecting a lens position that is either a near point-side lens position or a far point-side lens position based on the calculated phase difference, the near point-side lens position and the far point-side lens position being discrete lens positions set in advance; and changing a lens position of the imaging section to the lens position selected based on the phase difference.

BRIEF DESCRIPTION OF THE DRAWINGS

FIG. 3 illustrates an example of a look-up table according to the first embodiment.

FIG. 10 illustrates an example of a look-up table according to the second embodiment.

FIG. 14 illustrates a first example of a look-up table used for a phase detection AF process.

FIG. 15 illustrates a second example of a look-up table used for a phase detection AF process.

DESCRIPTION OF EXEMPLARY EMBODIMENTS

Figure 1:
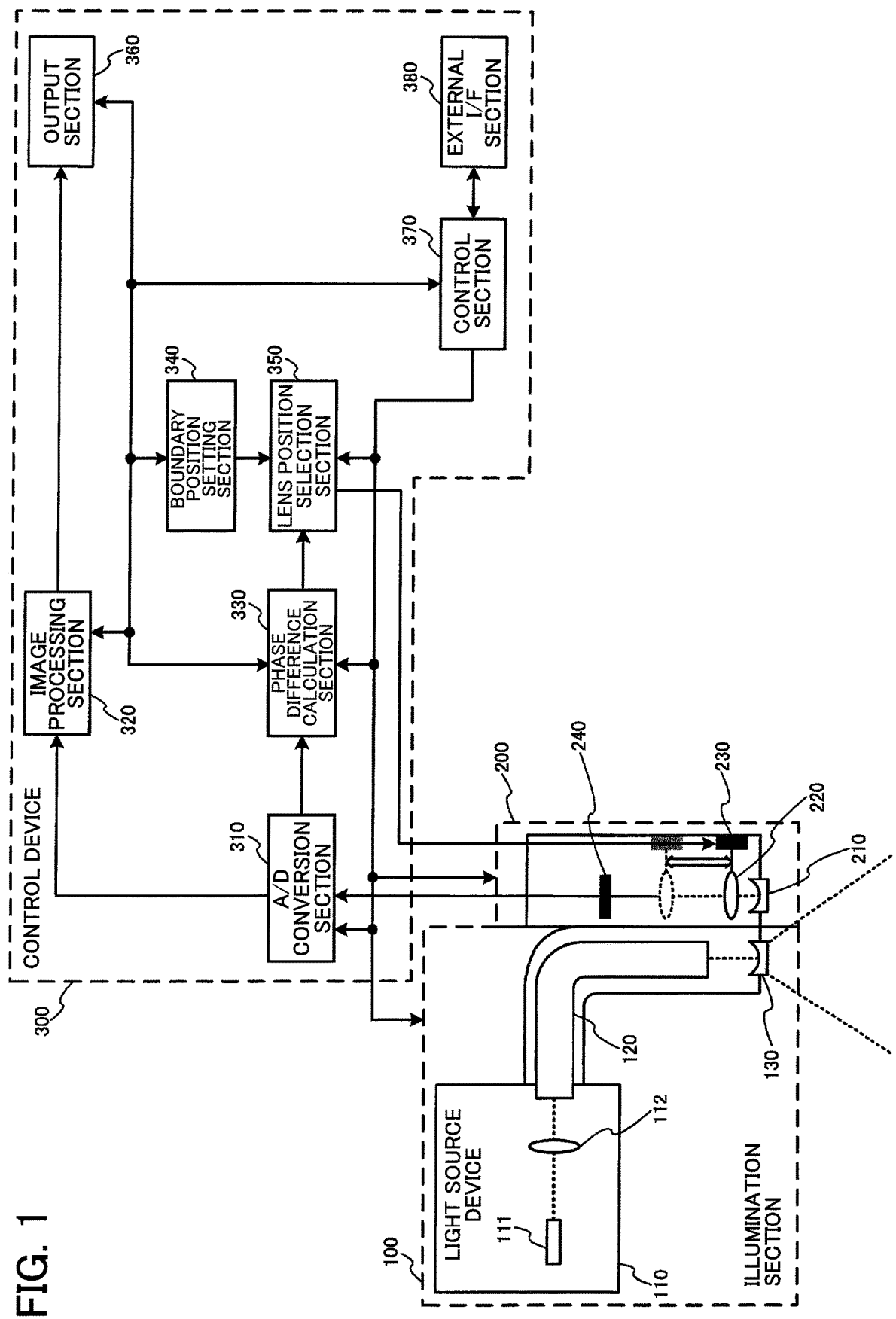
FIG. 1 illustrates a configuration example of an endoscope apparatus according to a first embodiment.

According to one embodiment of the invention, there is provided an endoscope apparatus comprising:

an imaging section that includes a phase difference detection element for implementing phase detection autofocus, and acquires a captured image;

a phase difference calculation section that calculates a phase difference based on a signal output from the phase difference detection element;

a lens position selection section that selects a lens position that is either a near point-side lens position or a far point-side lens position based on the phase difference, the near point-side lens position and the far point-side lens position being discrete lens positions set in advance; and a driver section that changes a lens position of the imaging section to the lens position selected by the lens position selection section.

According to one embodiment of the invention, the near point-side lens position or the far point-side lens position is selected based on the phase difference, and the lens position of the imaging section is changed to the selected lens position. Since one of the near point-side in-focus object plane position that corresponds to the near point-side lens position and the far point-side in-focus object plane position that corresponds to the far point-side lens position is selected, it is possible to suppress a change in the in-focus object plane position during the AF control process.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Outline

An outline of several embodiments of the invention is described below. It is desirable that an endoscope apparatus including an endoscope apparatus that performs an AF control process (see JP-A-2011-139760) have a deep depth of field so that the user can simultaneously observe the object over a wide range. When performing screening examination, the observation target area for the user repeatedly undergoes an in-focus state and a defocused state if the in-focus object plane position of the endoscope apparatus frequently and finely changes due to the AF control process. This may increase the burden imposed on the user (e.g., the user may have to continuously observe an identical area for a long time). Therefore, an AF control process that can reduce a change in the in-focus object plane position as much as possible is desired for the endoscope apparatus.

According to several embodiments of the invention, an endoscope apparatus is configured so that one of a near point-side in-focus object plane position NEAR and a far point-side in-focus object plane position FAR (see FIG. 2) that are set in advance can be selected. For example, the endoscope apparatus may be configured so that the depth of field (e.g., about 5 to about 70 mm) required for screening examination can be completely covered by the depth of field (e.g., about 5 to about 10 mm) when the near point-side in-focus object plane position NEAR is selected, and the depth of field (e.g., about 10 to about 70 mm) when the far point-side in-focus object plane position FAR is selected. It is possible to provide as deep a depth of field as possible at each in-focus object plane position by dividing the required depth of field into two parts, and selecting each in-focus object plane position.

In this case, the observation target area for the user can be brought into focus by merely performing the AF control process that selects one of the near point-side in-focus object plane position NEAR and the far point-side in-focus object plane position FAR. An image in which the object is in focus over a wide range can be acquired while merely selecting one of the two in-focus object plane positions during the AF control process as a result of implementing such an endoscope apparatus. This makes it possible to reduce the in-focus object plane position change frequency, and reduce the burden imposed on the user during screening examination as compared with a known contrast AF control process or the like that allows selection of a large number of in-focus object plane positions.

However, a problem may occur when determining the in-focus object plane position even when implementing the above AF control process. For example, a contrast AF control method may be employed that sequentially selects the near point-side in-focus object plane position NEAR and the far point-side in-focus object plane position FAR, calculates the contrast value from the image acquired corresponding to each in-focus object plane position, selects the in-focus object plane position at which a larger contrast value is obtained to be the target in-focus object plane position, and changes the in-focus object plane position of the endoscope apparatus to the target in-focus object plane position. According to this method, since it is necessary to continuously perform the AF control process that sequentially selects the near point-side in-focus object plane position NEAR and the far point-side in-focus object plane position FAR at an arbitrary timing, an in-focus state and a defocused state repeatedly occur when the AF control process is performed. This may increase the burden imposed on the user (e.g., the user may have to continuously observe an identical area for a long time).

According to several embodiments of the invention, an image sensor that detects the phase difference is provided in the endoscope apparatus. The near point-side in-focus object plane position NEAR or the far point-side in-focus object plane position FAR is selected corresponding to phase difference information obtained from the image sensor, and the AF control process is performed. According to the above configuration, since the distance from the imaging section to the object can be determined based on the phase difference information, an appropriate in-focus object plane position can be selected from the near point-side in-focus object plane position NEAR and the far point-side in-focus object plane position FAR (i.e., it is unnecessary to sequentially select the near point-side in-focus object plane position NEAR and the far point-side in-focus object plane position FAR, determine the degree of in-focus state, and then select the near point-side in-focus object plane position NEAR or the far point-side in-focus object plane position FAR). When acquiring the contrast value while sequentially selecting the near point-side in-focus object plane position NEAR and the far point-side in-focus object plane position FAR, an in-focus state and a defocused state necessarily occur. According to several embodiments of the invention, however, it is unnecessary to select an in-focus object plane position at which a defocused state occurs. This makes it possible to provide an endoscope apparatus that automatically suppresses a situation in which the observation target area for the user is out of focus, and reduces the burden imposed on the user in terms of observation and operation.

2. First Embodiment

2.1. Endoscope Apparatus

A first embodiment of the invention is described in detail below. FIG. 1 illustrates a configuration example of an endoscope apparatus according to the first embodiment. The endoscope apparatus illustrated in FIG. 1 includes an illumination section 100 that emits illumination light, an imaging section 200 that images (captures) the object, and a control device 300 (processing section) that controls each section of the endoscope apparatus.

The illumination section 100 includes a light source device 110 that includes a white light source 111 and a condenser lens 112, and a light guide fiber 120, and an illumination optical system 130. The imaging section 200 includes a condenser lens 210, a focus lens 220, a focus lens driver section 230, and an image sensor 240. The focus lens driver section 230 is implemented by a voice coil motor (VCM), for example. The control device 300 includes an A/D conversion section 310, an image processing section 320, a phase difference calculation section 330, a boundary position setting section 340, a lens position selection section 350, an output section 360, a control section 370, and an external I/F section 380. The control section 370 includes a microcomputer, a CPU, and the like. The external I/F section 380 includes a power switch, a variable setting interface, and the like.

The operation of the endoscope apparatus illustrated in FIG. 1 is described below. The white light source 111 emits white light. The white light reaches the condenser lens 112, and is focused by the condenser lens 112. The focused white light passes through the light guide fiber 120, and is applied to the object from the illumination optical system 130. The white light reflected from the object is focused by the condenser lens 210, passes through the focus lens 220, and forms an image on the image sensor 240. The image sensor 240 performs a photoelectric conversion process to acquire an analog signal.

Figure 2:
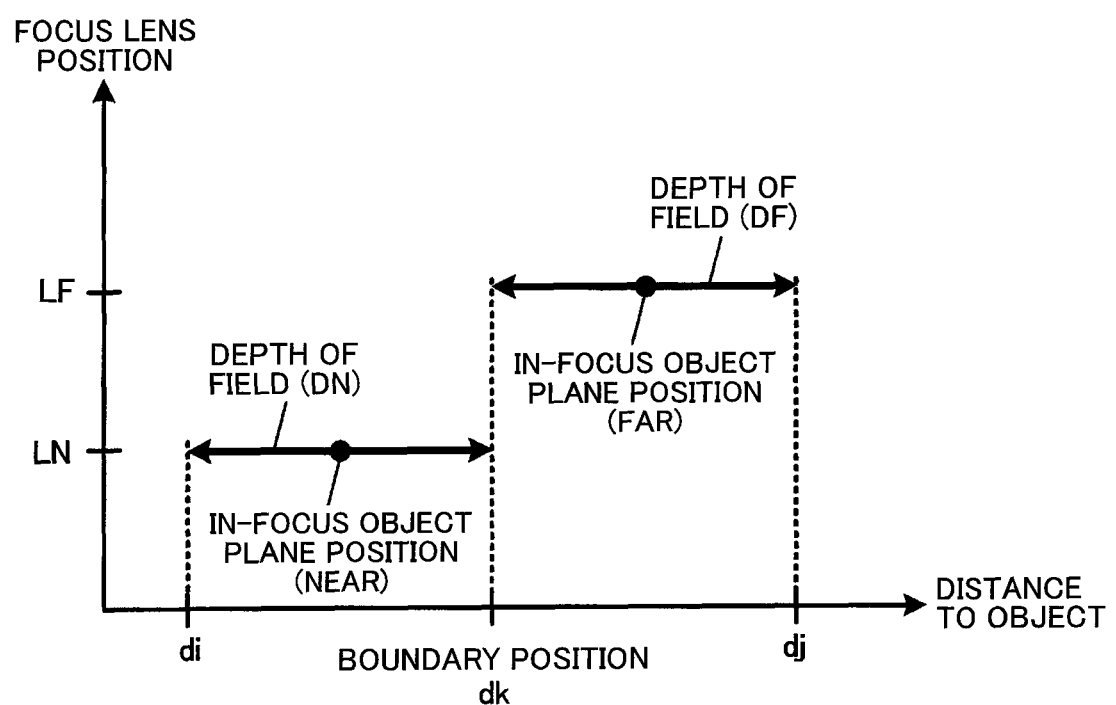
FIG. 2 is a view illustrating the operation of a focus lens driver section according to the first embodiment.

The focus lens 220 is driven by the focus lens driver section 230 between two points (LN and LF) along the optical axis (described later with reference to FIG. 2). The focus lens driver section 230 drives the focus lens 220 to the position selected by the lens position selection section 350 (described later with reference to FIG. 3 and the like). The image sensor 240 includes a phase difference detection element in its pixel array (described later with reference to FIG. 12 and the like). The A/D conversion section 310 converts the analog signal acquired by the image sensor 240 into a digital signal. The digital signal includes a captured image obtained from an imaging pixel and a phase signal obtained from the phase difference detection element.

The image processing section 320 performs image processing (e.g., interpolation process and grayscale transformation process) on the captured image output from the A/D conversion section 310.

The phase difference calculation section 330 calculates the phase difference based on the phase signal output from the A/D conversion section 310 (described later with reference to FIG. 14 and the like). The boundary position setting section 340 sets a (phase difference) boundary position dk (described later with reference to FIG. 3 and the like). The lens position selection section 350 compares the phase difference calculated by the phase difference calculation section 330 with the boundary position set by the boundary position setting section 340. The lens position selection section 350 determines whether to move the focus lens 220 to the near point-side lens position LN or the far point-side lens position LF, and transmits information about the determined lens position to the focus lens driver section 230.

The output section 360 displays the captured image subjected to image processing by the image processing section 320 on a display (not illustrated in the drawings), or stores the captured image in a recording medium (e.g., memory card) (not illustrated in the drawings).

2.2. Focus Lens Driver Section

The operation of the focus lens driver section 230 is described in detail below with reference to FIG. 2. The focus lens driver section 230 moves the focus lens 220 to the discrete lens position LN or LF to change the in-focus object plane position to the in-focus object plane position NEAR or FAR (see FIG. 2).

More specifically, the focus lens driver section 230 changes the position of the focus lens 220 to the lens position LN that corresponds to the in-focus object plane position NEAR (near point) that is close to the imaging section 200, or the lens position LF that corresponds to the in-focus object plane position FAR (far point) that is distant from the imaging section 200. The depth of field DN (di to dk) when the near point-side in-focus object plane position is selected is normally shallow, and the object easily lies outside the depth of field even when the object has moved to only a small extent. Therefore, the near point-side in-focus object plane position is suitable when closely observing a shallow object. In contrast, the depth of field DN (dk to dj) when the far point-side in-focus object plane position is selected is deep. Therefore, the far point-side in-focus object plane position is suitable when screening a hollow tubular object. The depth of field required for endoscopic observation is achieved by changing the position of the focus lens. For example, the depth of field (di to dj) that can be implemented by combining the depth of field DN and the depth of field DF includes the range of 2 to 70 mm.

The term "in-focus object plane position" used herein refers to the position of the object at which the imaging section 200 can bring the object into focus. For example, the in-focus object plane position is indicated by the distance to the object from the end of the imaging section 200 along the optical axis of the imaging optical system. More specifically, the term "in-focus object plane position" used herein refers to the position of the object plane that corresponds to the image plane when the light-receiving plane of the image sensor 240 coincides with the image plane. Since the object is considered to be in focus as long as the object lies within the depth of field of the imaging section 200, the in-focus object plane position may be set to an arbitrary position within the depth of field. For example, the in-focus object plane position NEAR and the in-focus object plane position FAR illustrated in FIG. 2 may be set to an arbitrary position within the depth of field DN and the depth of field DF, respectively. In this case, the in-focus object plane position and the depth of field are also changed by changing the position of the focus lens 220.

The term "position" used herein in connection with the focus lens 220 refers to the position of the focus lens 220 (movable lens) in the imaging optical system. For example, the position of the focus lens 220 is indicated by the distance to the focus lens 220 from a reference point in the imaging optical system. The reference point may be the position of the lens of the imaging optical system that is positioned closest to the object, the position of the light-receiving plane of the image sensor 240, or the like.

In the first embodiment, a zoom magnification adjustment and a focus adjustment may be implemented by driving only the focus lens, or the zoom lens and the focus lens may be independently adjusted.

2.3. AF Control Method

An AF control method according to the first embodiment is described in detail below.

A look-up table (see FIG. 3) in which the phase difference and the distance to the object are linked is provided in advance. The look-up table is stored in a storage section (not illustrated in the drawings) included in the lens position selection section 350, for example. Since the phase difference corresponding to an identical distance differs between the in-focus object plane position NEAR and the in-focus object plane position FAR, the relationship between the phase difference and the distance at the in-focus object plane position NEAR and the relationship between the phase difference and the distance at the in-focus object plane position FAR are stored in the look-up table. The lens position selection section 350 acquires the distance corresponding to the phase difference calculated by the phase difference calculation section 330 from the look-up table to calculate the distance to the object from the imaging section.

Note that the AF control method according to the first embodiment need not necessarily utilize the look-up table. For example, the distance to the object may be calculated by the following expression (1). Note that d is the distance to the object, p is the phase difference, and $\alpha$ and $\beta$ are predetermined constants.

$$d = \alpha \cdot p + \beta \quad (1)$$

The near point-side lens position LN and the far point-side lens position LF (see FIG. 2) are set in advance. As illustrated in FIG. 3, the position of the focus lens at which the object is brought into focus when the distance to the object is within the range of di to dk (di<dk) (depth of field DN) is set to be the lens position LN. The position of the focus lens at which the object is brought into focus when the distance to the object is within the range of dk to dj (dk<dj) (depth of field DF) is set to be the lens position LF. It is possible to provide an image in which the object is in focus when the distance to the object is within the range of di to dj by appropriately changing the lens position to the lens position LN or the lens position LF. In other words, two positions to which the focus lens is moved are set to the lens position LN and the lens position LF when it is desired to provide an image in which the object is in focus when the distance to the object is within the range of di to dj.

The boundary position setting section 340 sets the boundary position dk in advance based on the information about the depth of field. As illustrated in FIG. 2, the boundary position dk corresponds to the boundary between the depth of field DN and the depth of field DF, and is indicated by the distance from the end of the imaging section 200, for example. Note that the boundary position setting section 340 may set the boundary position dk based on a boundary position that has been set via the external I/F section 380.

The lens position selection section 350 compares the distance to the object that corresponds to the phase difference with the boundary position dk set by the boundary position setting section 340. The lens position selection section 350 selects the near point-side lens position LN when the distance to the object is equal to or shorter than the boundary position dk. The lens position selection section 350 selects the far point-side lens position LF when the distance to the object is longer than the boundary position dk.

The lens position selection section 350 stores information that indicates whether the current position of the focus lens 220 is the near point-side lens position LN or the far point-side lens position LF. When the in-focus object plane position FAR has been selected when the current position of the focus lens 220 is the near point-side lens position LN, the lens position selection section 350 instructs the focus lens driver section 230 to move the focus lens 220 to the far point-side lens position LF. The focus lens driver section 230 receives the instruction information, and moves the focus lens 220 to the far point-side lens position LF. When the in-focus object plane position NEAR has been selected when the current position of the focus lens 220 is the far point-side lens position LF, the lens position selection section 350 instructs the focus lens driver section 230 to move the focus lens 220 to the near point-side lens position LN. The focus lens driver section 230 receives the instruction information, and moves the focus lens 220 to the near point-side lens position LN.

The above AF control method can change the lens position based on the phase difference by converting the phase difference into distance using the look-up table, and comparing the distance with the boundary position dk. Since the lens position is determined by comparing the distance with the boundary position dk, it is unnecessary to change the lens position to the lens position LN and the lens position LF (i.e., contrast AF method).

When the object moves across the boundary position dk when the object lies in the vicinity of the boundary position dk, the lens position may be frequently changed between the lens position LN and the lens position LF. In this case, since the position of the focus lens 220 frequently changes, the angle of view of the image presented to the user frequently changes, and makes observation difficult. In order to prevent such a situation, the lens position selection section 350 may not compare the distance to the object with the boundary position until a given time elapses after the lens position has been changed to the lens position LN or the lens position LF. Alternatively, the lens position selection section 350 may select the lens position LF when it has been continuously determined that the distance to the object is longer than the boundary position dk for a given time in a state in which the lens position LN is selected, and may select the lens position LN when it has been continuously determined that the distance to the object is shorter than the boundary position dk for a given time in a state in which the lens position LF is selected.

2.4. Second AF Control Method

Although FIG. 3 illustrates an example in which the phase difference is converted into distance, and the distance is compared with the boundary position dk, the configuration is not limited thereto. Since the phase difference and the distance to the object have a correlation, the phase difference may be compared directly with the boundary position. An AF control method that directly utilizes the phase difference is described below.

Figure 4A:
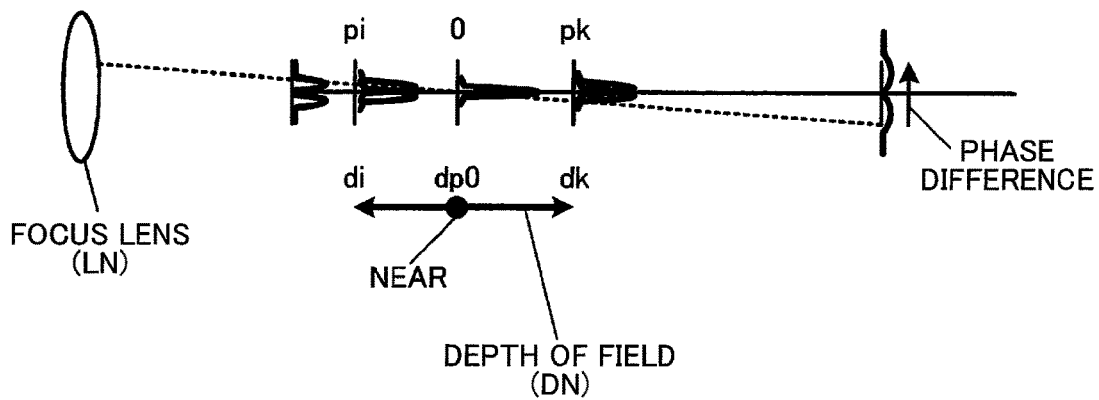
FIG. 4A is a schematic view illustrating a phase difference when a focus lens is set to a near point-side position.

FIG. 4A schematically illustrates the phase difference when the focus lens is set to the near point-side lens position LN. A signal of a first-pupil object image and a signal of a second-pupil object image are obtained from the phase difference detection element. When the object lies at the distance dp0 (in-focus object plane position NEAR), the phase difference between the first-pupil object image and the second-pupil object image is zero. The phase difference (i.e., the absolute value of the phase difference) between the first-pupil object image and the second-pupil object image increases as the distance to the object increases or decreases from the distance dp0. The phase difference calculation section 330 acquires the phase difference by calculating the distance (phase difference) between the two peaks via correlation calculations or the like. Note that the following description is given on the assumption that the phase difference when the distance to the object is longer than the distance dp0 is positive.

Figure 4B:
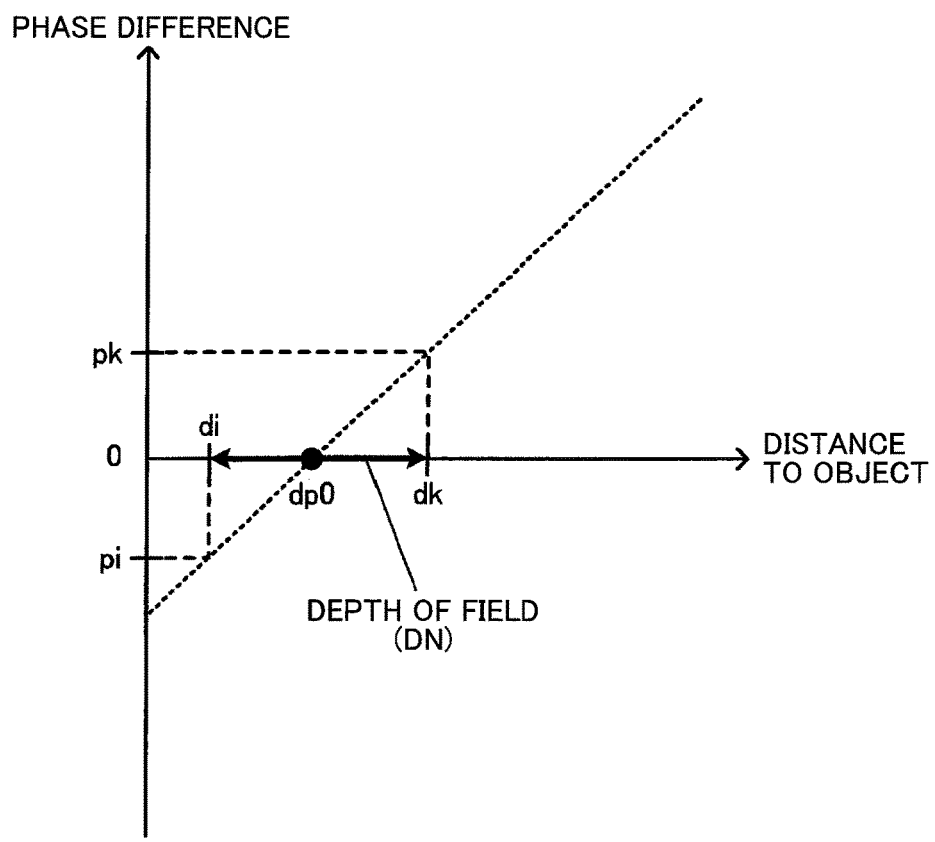
FIG. 4B illustrates an example of phase difference characteristics when a focus lens is set to a near point-side position.

FIG. 4B illustrates an example of the phase difference characteristics with respect to the distance to the object when the focus lens is set to the near point-side lens position LN. As illustrated in FIG. 4B, the phase difference has linear characteristics with respect to the distance to the object. The phase difference "0" corresponds to the distance dp0 at the in-focus object plane position NEAR, and the phase difference pi to pk corresponds to the distance di to dk within the depth of field DN. The first phase difference pk corresponds to the boundary position dk. The boundary position setting section 340 sets the first phase difference pk in advance. The lens position selection section 350 maintains the focus lens 220 at the near point-side lens position LN when the phase difference calculated by the phase difference calculation section 330 is equal to or smaller than the first phase difference pk in a state in which the near point-side lens position LN is selected, and selects the far point-side lens position LF when the phase difference calculated by the phase difference calculation section 330 is larger than the first phase difference pk in a state in which the near point-side lens position LN is selected.

Figure 5A:
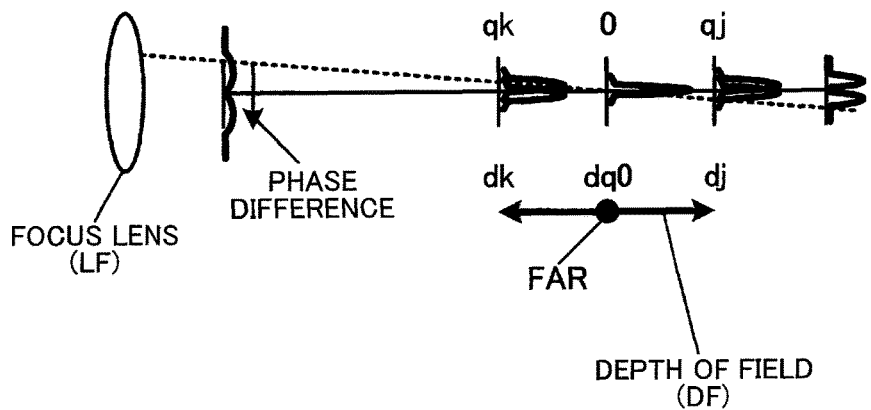
FIG. 5A is a schematic view illustrating a phase difference when a focus lens is set to a far point-side position.
Figure 5B:
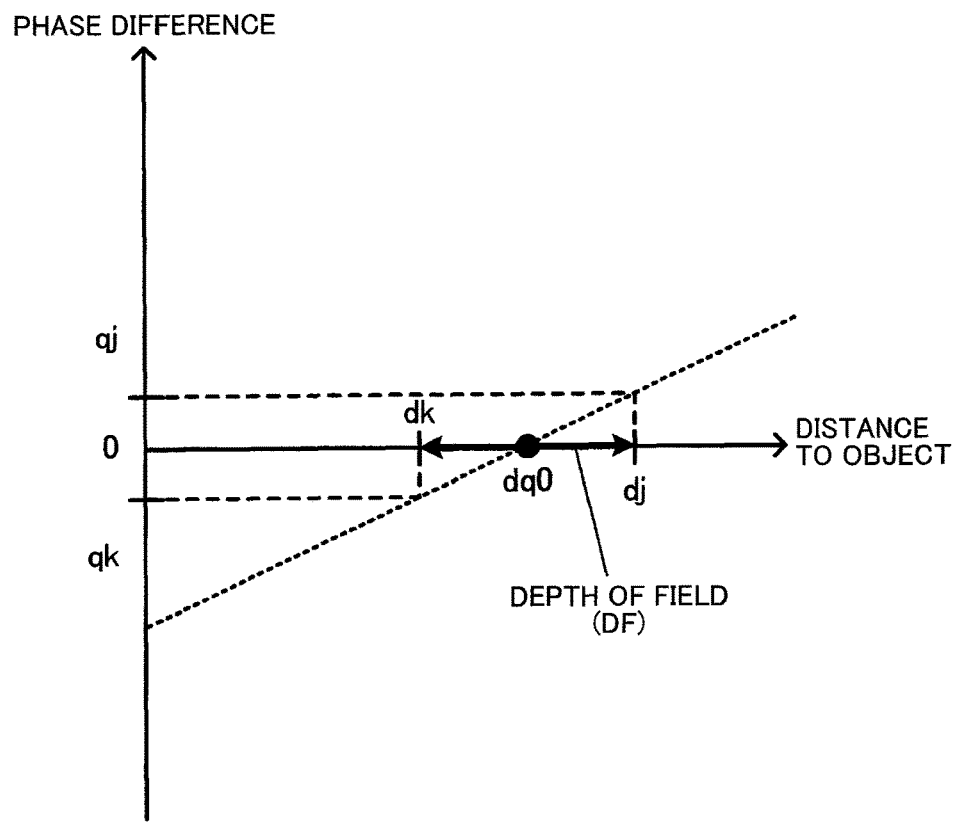
FIG. 5B illustrates an example of phase difference characteristics when a focus lens is set to a far point-side position.

FIG. 5A schematically illustrates the phase difference when the focus lens is set to the far point-side lens position LF. FIG. 5B illustrates an example of the phase difference characteristics with respect to the distance to the object when the focus lens is set to the far point-side lens position LF. As illustrated in FIGS. 5A and 5B, the phase difference "0" corresponds to the distance dp0 at the in-focus object plane position FAR, and the phase difference pk to pj corresponds to the distance dk to dj within the depth of field DR The second phase difference qk corresponds to the boundary position dk. The boundary position setting section 340 sets the second phase difference qk in advance. The lens position selection section 350 maintains the focus lens 220 at the far point-side lens position LF when the phase difference calculated by the phase difference calculation section 330 is equal to or larger than the second phase difference qk in a state in which the far point-side lens position LF is selected, and selects the near point-side lens position LN when the phase difference calculated by the phase difference calculation section 330 is smaller than the second phase difference qk in a state in which the far point-side lens position LF is selected.

The above AF control method can determine the lens position by comparing the phase difference directly with the phase difference pk or qk corresponding to the boundary position dk without converting the phase difference into another value (e.g., distance). This makes it possible to implement the AF control process using a simple process as compared with the case of converting the phase difference into another value.

2.5. AF Control Method when Phase Difference is not Detected

An AF control method when the phase difference calculation section 330 could not detect the phase difference is described below.

Figure 6:
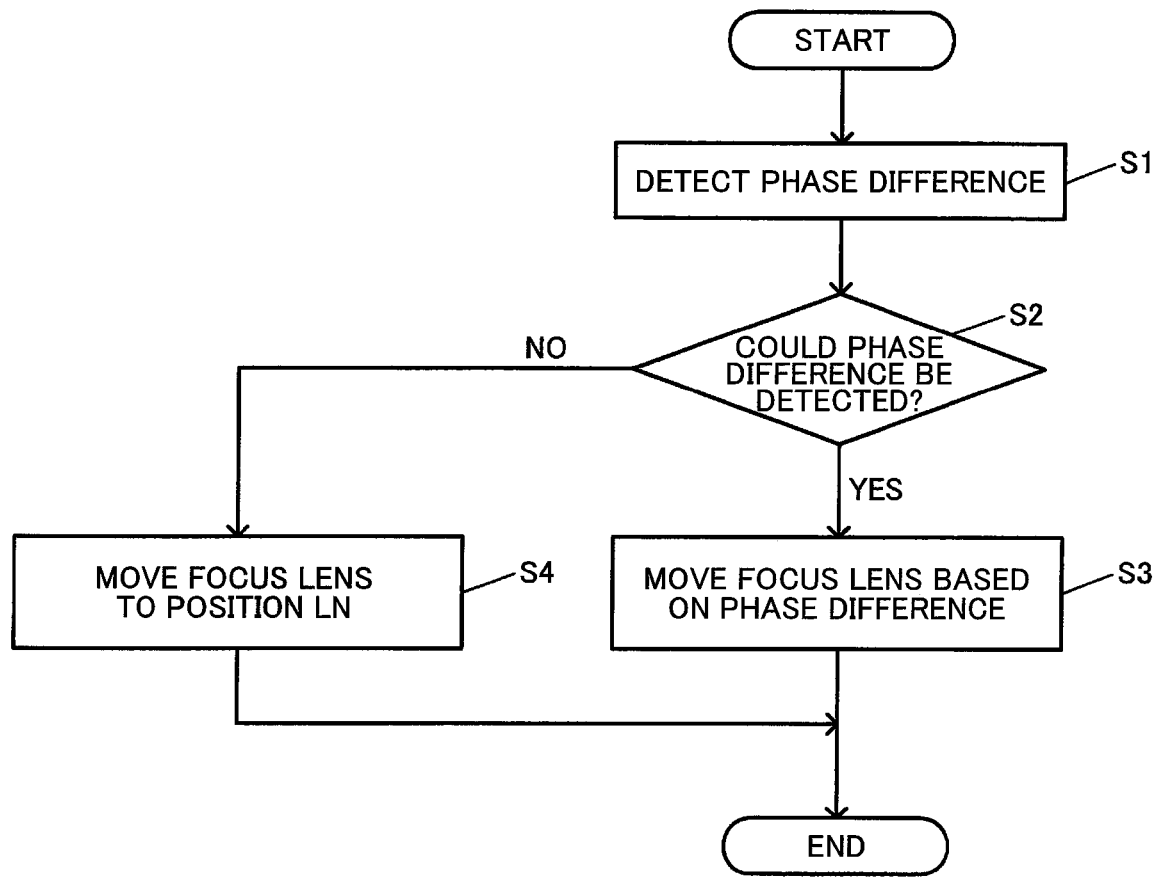
FIG. 6 illustrates a first flowchart of an AF control process.

FIG. 6 illustrates a first flowchart of the AF control process. When the AF control process has started, the phase difference calculation section 330 detects (calculates) the phase difference (S1). The lens position selection section 350 determines whether or not the phase difference calculation section 330 could detect (calculate) the phase difference (S2). It may be impossible to detect (calculate) the phase difference when the distance to the object is very short (i.e., when the object and the condenser lens 210 are positioned very close to each other). When the phase difference calculation section 330 could not detect the phase difference, the phase difference calculation section 330 outputs a non-detection signal that indicates that the phase difference calculation section 330 could not detect the phase difference. When the lens position selection section 350 has received the non-detection signal, the lens position selection section 350 determines that the phase difference calculation section 330 could not detect (calculate) the phase difference.

Figure 12:
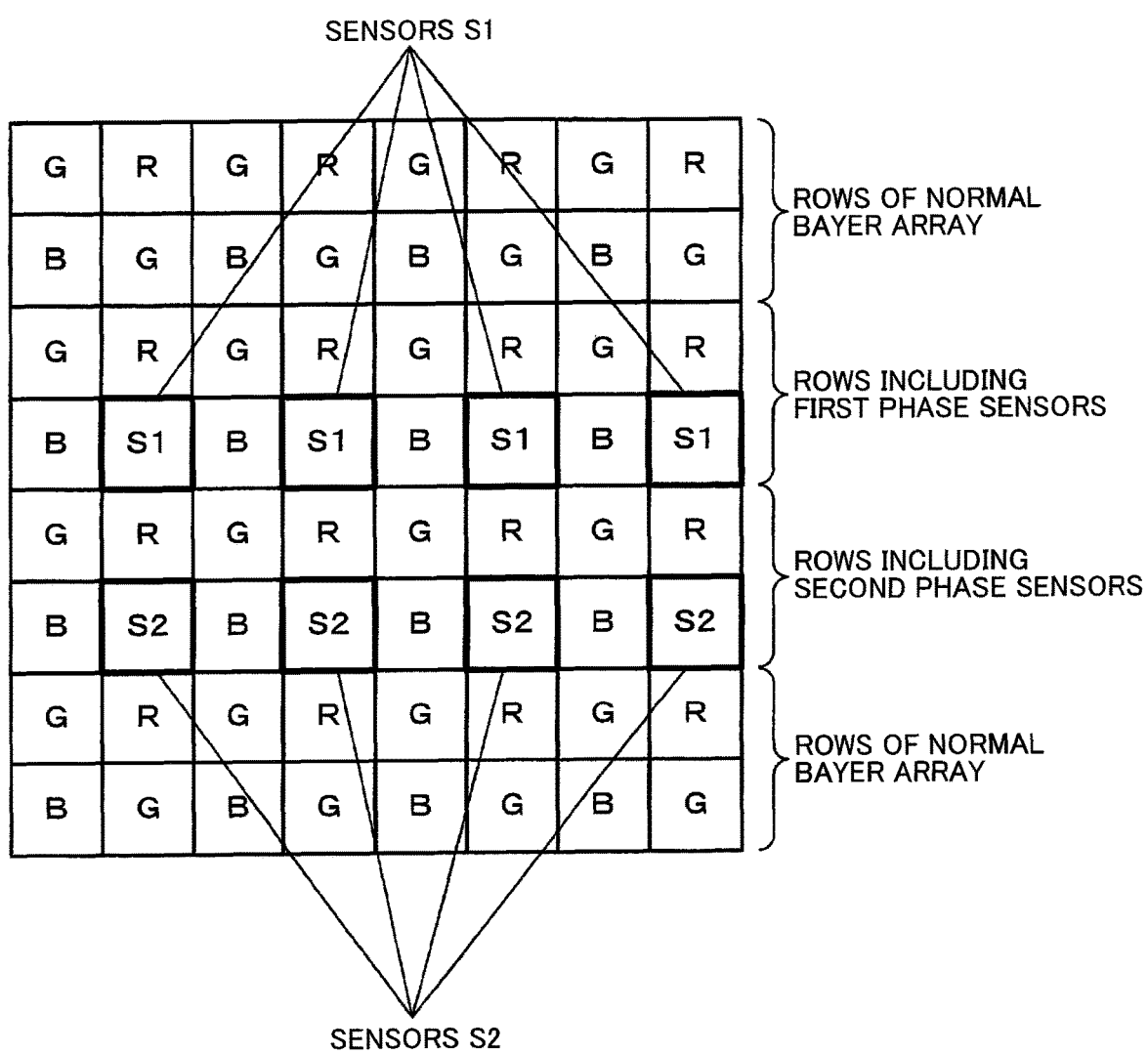
FIG. 12 illustrates a configuration example of an image sensor that is provided with a phase difference detection element.

The phase difference calculation section 330 determines that the phase difference could not be detected when the first-pupil object image or the second-pupil object image is out of focus. For example, the phase difference calculation section 330 determines that the phase difference could not be detected when the maximum value of the phase signal described with reference to FIG. 4A is equal to or smaller than a given threshold value. The phase difference calculation section 330 may determine that the phase difference could not be detected when the difference between the maximum value and the minimum value of the phase signals obtained from the phase difference sensors S1 (or S2) illustrated in FIG. 12 is equal to or smaller than a given threshold value. The phase difference calculation section 330 may determine that the phase difference could not be detected when the distribution of the first-pupil object image or the second-pupil object image is flat. For example, the phase difference calculation section 330 may determine that the phase difference could not be detected when the standard deviation of the phase signals obtained from the phase difference sensors S1 (or S2) is equal to or smaller than a given threshold value. The phase difference calculation section 330 may determine that the phase difference could not be detected when the distance between the first-pupil object image and the second-pupil object image is too long. For example, the phase difference calculation section 330 may determine that the phase difference could not be detected when the distance between the pixel position that corresponds to the maximum value of the phase signals obtained from the phase difference sensors S1 and the pixel position that corresponds to the maximum value of the phase signals obtained from the phase difference sensors S2 is longer than a given distance.

When the lens position selection section 350 has determined that the phase difference calculation section 330 could detect (calculate) the phase difference in the step S2, the lens position selection section 350 determines the lens position based on the phase difference, and the focus lens driver section 230 moves the focus lens to the determined lens position (S3). When the lens position selection section 350 has determined that the phase difference calculation section 330 could not detect (calculate) the phase difference in the step S2, the lens position selection section 350 sets the distance to the object to "0", and compares the distance "0" with the boundary position dk to select the near point-side lens position LN. When the current lens position is the far point-side lens position LF, the focus lens driver section 230 moves the focus lens to the near point-side lens position LN (S4).

It is considered that the imaging section is positioned close to the object when the phase difference cannot be detected. Specifically, since the endoscope apparatus is used to observe a narrow space inside a body, the optical system of the endoscope apparatus is normally designed so that a distance of several ten mm or more from the end of the imaging section is almost equivalent to infinity, and the in-focus object plane position FAR is close to infinity. Therefore, it is inconceivable that the object image is out of focus, and the phase difference cannot be detected when the object is positioned away from the imaging section. It is likely that the phase difference cannot be detected when the object is positioned close to the imaging section. Since the AF control process illustrated in FIG. 6 sets the distance to "0" when the phase difference could not be detected, an appropriate in-focus object plane position (NEAR) can be selected from the in-focus object plane position NEAR and the in-focus object plane position FAR.

Figure 7:
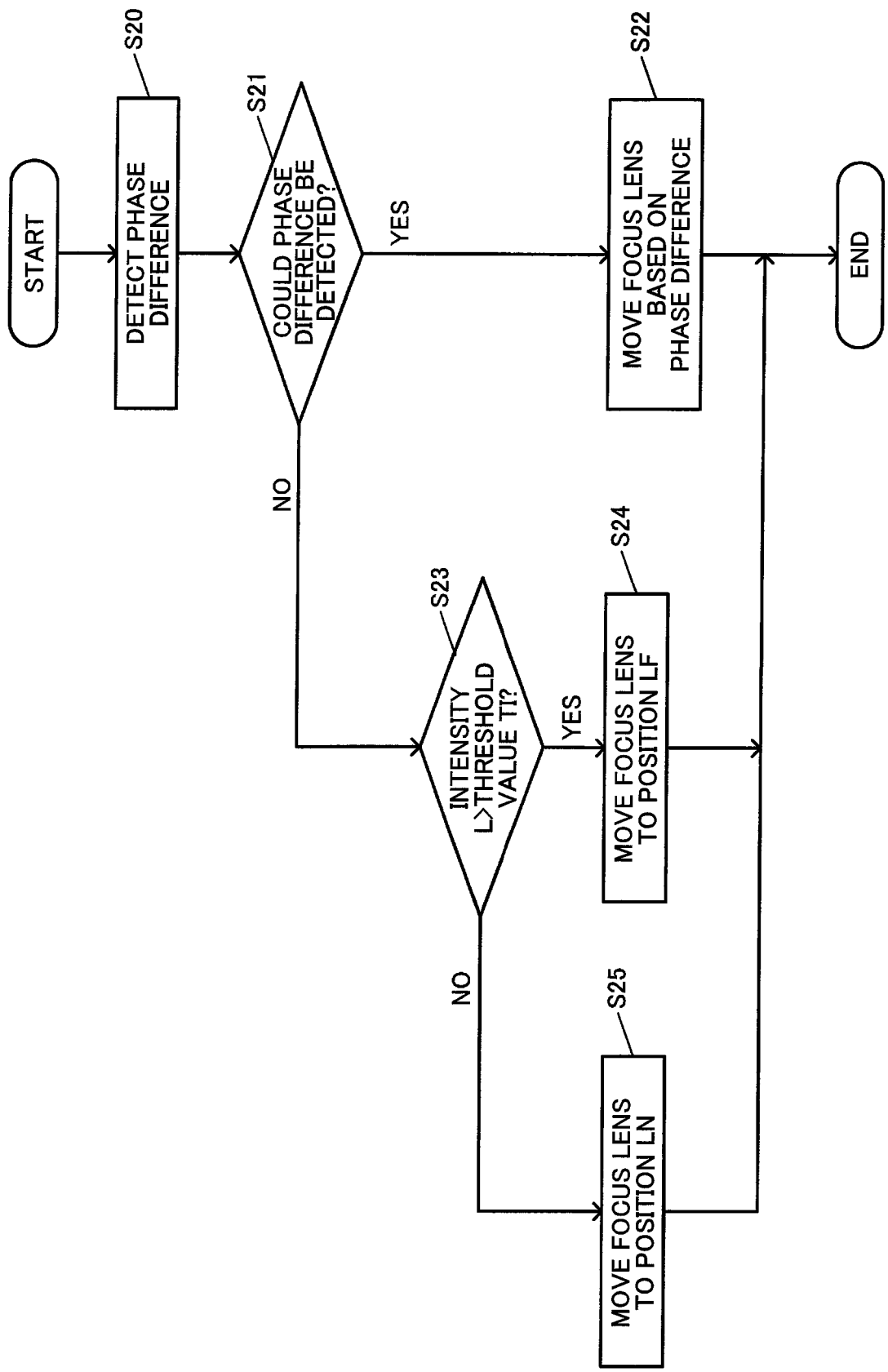
FIG. 7 illustrates a second flowchart of an AF control process.

FIG. 7 illustrates a second flowchart of the AF control process. The AF control process illustrated in FIG. 7 selects the lens position based on the intensity of illumination light when the phase difference could not be detected.

Specifically, when the AF control process has started, the phase difference calculation section 330 detects (calculates) the phase difference (S20). When the lens position selection section 350 has determined that the phase difference calculation section 330 could detect (calculate) the phase difference (S21, YES), the lens position selection section 350 determines the lens position based on the phase difference, and the focus lens driver section 230 moves the focus lens to the determined lens position (S22).

When the lens position selection section 350 has determined that the phase difference calculation section 330 could not detect (calculate) the phase difference (S21, NO), the lens position selection section 350 acquires information about the intensity L of illumination light from the control section 370. The intensity of illumination light applied to the object by the illumination section 100 is controlled by the control section 370, and the information about the intensity L corresponds to a control signal output from the control section 370. For example, the information about the intensity L is information about the degree of opening of an aperture (not illustrated in the drawings) that adjusts the intensity. When the light source is an LED of which the intensity is determined by the amount of current, the information about the intensity L is information about the amount of current that is caused to flow through the LED. The lens position selection section 350 compares the intensity L with a threshold value TI (S23), and selects the far point-side lens position LF when the lens position selection section 350 has determined that the intensity L is larger than the threshold value TI. The focus lens driver section 230 then moves the focus lens to the far point-side lens position LF (S24). The lens position selection section 350 selects the near point-side lens position LN when the lens position selection section 350 has determined that the intensity L is equal to or smaller than the threshold value TI, and the focus lens driver section 230 moves the focus lens to the near point-side lens position LN (S25).

It may be impossible for the endoscope apparatus to detect the phase difference when the contrast of a mucous membrane of an internal organ or the like is low. The intensity of illumination light applied by the endoscope apparatus is normally adjusted so that the brightness of the image is constant. Since the object is brightly illuminated when the object is positioned close to the imaging section, the brightness of the image is made constant by decreasing the intensity of illumination light when the object is positioned close to the imaging section. The AF control process illustrated in FIG. 7 can select the in-focus object plane position based on the intensity of illumination light by utilizing such a dimming control process.

Figure 8:
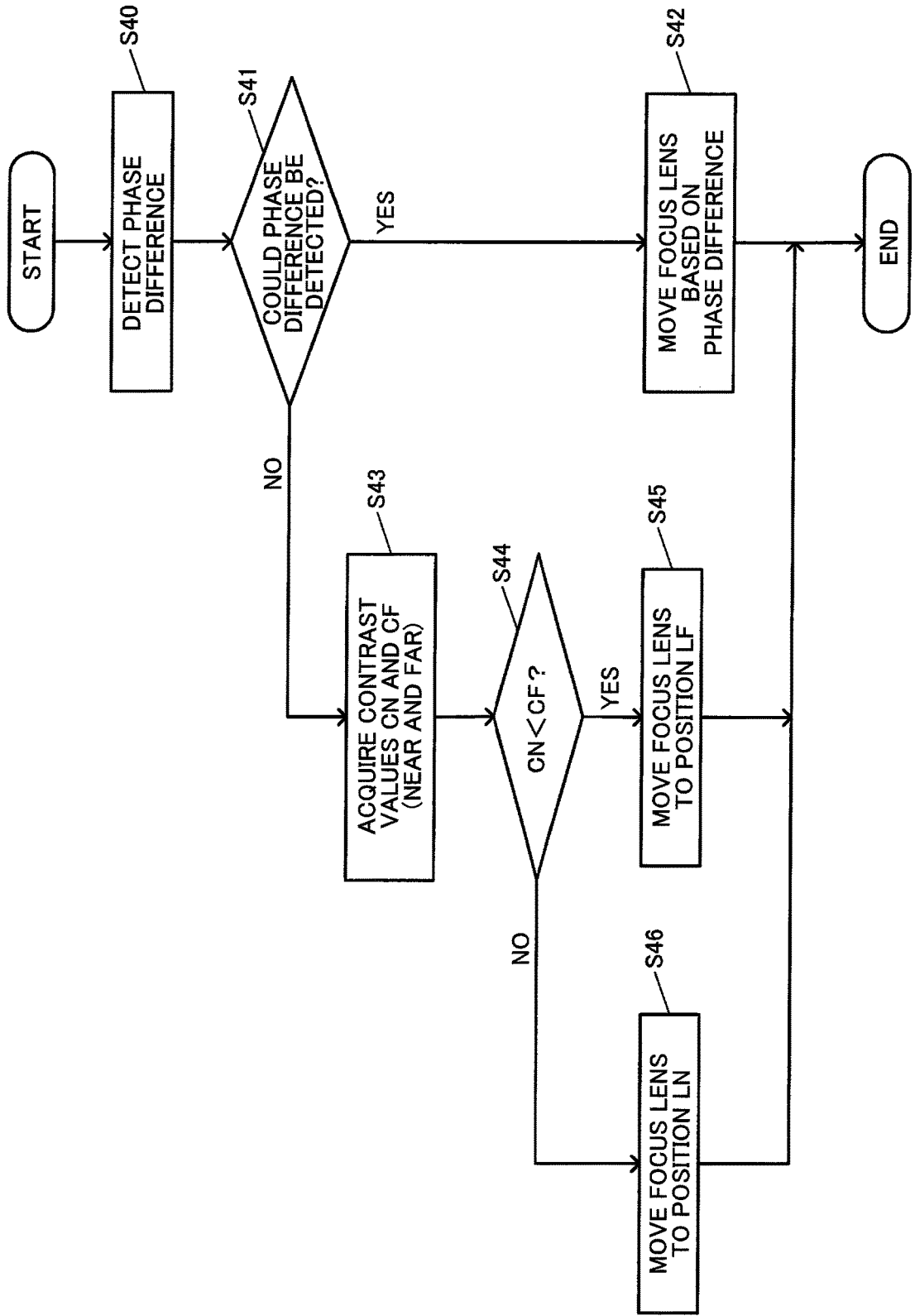
FIG. 8 illustrates a third flowchart of an AF control process.

FIG. 8 illustrates a third flowchart of the AF control process. The AF control process illustrated in FIG. 8 utilizes a contrast AF control process when the phase difference could not be detected. It is possible to bring the object into focus even when the phase difference could not be detected by utilizing the contrast AF control process. Specifically, when the AF control process has started, the phase difference calculation section 330 detects (calculates) the phase difference (S40). When the lens position selection section 350 has determined that the phase difference calculation section 330 could detect (calculate) the phase difference (S41, YES), the lens position selection section 350 determines the lens position based on the phase difference, and the focus lens driver section 230 moves the focus lens to the determined lens position (S42).

When the lens position selection section 350 has determined that the phase difference calculation section 330 could not detect (calculate) the phase difference (S41, NO), the lens position selection section 350 sequentially selects the lens position LN and the lens position LF, and the focus lens driver section 230 sequentially moves the focus lens to the near point-side lens position LN and the far point-side lens position LF. The phase difference calculation section 330 calculates a first contrast value CN from the image captured at the near point-side lens position LN (in-focus object plane position NEAR), and calculates a second contrast value CF from the image captured at the far point-side lens position LF (in-focus object plane position FAR) (S43). The lens position selection section 350 compares the first contrast value CN with the second contrast value CF (S44). The lens position selection section 350 selects the far point-side lens position LF when the first contrast value CN is smaller than the second contrast value CF, and the focus lens driver section 230 moves the focus lens to the far point-side lens position LF (S45). The lens position selection section 350 selects the near point-side lens position LN when the first contrast value CN is equal to or larger than the second contrast value CF, and the focus lens driver section 230 moves the focus lens to the near point-side lens position LN (S46).

According to the first embodiment, the endoscope apparatus includes the imaging section 200, the phase difference calculation section 330, the lens position selection section 350, and a driver section (focus lens driver section 230) (see FIG. 1). The imaging section 200 includes the phase difference detection element (e.g., S1 and S2 in FIG. 12) for implementing phase detection autofocus, and acquires a captured image. The phase difference calculation section 330 calculates the phase difference based on the signal output from the phase difference detection element. As described above with reference to FIG. 2 and the like, the lens position selection section 350 selects a lens position that is either the near point-side lens position or the far point-side lens position based on the phase difference, the near point-side lens position and the far point-side lens position being discrete lens positions set in advance. The driver section changes the lens position of the imaging section to the lens position selected by the lens position selection section.

The above configuration makes it possible to suppress a change in the in-focus object plane position during the AF control process, and suppress a situation in which a burden is imposed on the user (i.e., the depth of field or the zoom magnification changes) due to a frequent change in the in-focus object plane position. Specifically, since the focus lens is moved to the discrete lens position LN or LF, the in-focus object plane position change frequently can be reduced as compared with the case where the focus lens is moved to a larger number of lens positions. Since the lens position is selected based on the phase difference, the lens position can be determined without causing the focus lens to make a round trip between the lens positions LN and LF. When it is necessary to cause the focus lens to make a round trip between the lens positions LN and LF in order to determine the lens position, it is necessary to cause the focus lens to make a round trip between the lens positions LN and LF even when the current lens position is maintained. According to the first embodiment, it is possible to prevent a situation in which the focus lens makes an unnecessary round trip between the lens positions.

According to the first embodiment, since the depth of field required for the endoscope apparatus is covered by the depth of field DN and the depth of field DF that respectively correspond to the in-focus object plane position NEAR and the in-focus object plane position FAR, it is possible to increase each depth of field as compared with the case of dividing the depth of fields into a larger number of parts, and provide an image that facilitates observation when examining a deep affected area.

The endoscope apparatus may include the boundary position setting section 340 that sets the boundary position between the near point-side in-focus object plane position NEAR that corresponds to the near point-side lens position LN and the far point-side in-focus object plane position FAR that corresponds to the far point-side lens position LF. As described above with reference to FIGS. 3 to 5B, the lens position selection section 350 may select the near point-side lens position LN when the lens position selection section 350 has determined that the position of the object corresponding to the phase difference (e.g., the distance to the object from the end of the imaging section 200) is closer to the imaging section 200 than the boundary position dk, and may select the far point-side lens position LF when the lens position selection section 350 has determined that the position of the object corresponding to the phase difference is farther from the imaging section 200 than the boundary position dk.

This makes it possible to select the lens position LN or LF based on the phase difference. Since whether the object is positioned on the near point side or the far point side can be determined based on the boundary position dk, the current lens position is maintained until the position of the object changes across the boundary position dk, and a frequent change in the in-focus object plane position can be suppressed.

The boundary position setting section 340 may set the boundary position dk at the boundary between the depth of field DN when the near point-side lens position LN is selected and the depth of field DF when the far point-side lens position LF is selected.

According to the above configuration, since an area in which the object is not brought into focus does not exist between the depth of field DN and the depth of field DF, an in-focus state can necessarily be obtained within the deep-focus depth of field (di to dj) required for the endoscope apparatus by selecting the lens position LN or LF. It is also possible to determine whether the object lies within the depth of field DN or the depth of field DF by setting the boundary position dk at the boundary between the depth of field DN and the depth of field DF, and select an appropriate lens position at which the object is brought into focus.

The driver section (focus lens driver section 230) may maintain the current lens position of the imaging section 200 for a given time after changing the lens position of the imaging section from the near point-side lens position LN to the far point-side lens position LF, or changing the lens position of the imaging section from the far point-side lens position LF to the near point-side lens position LN.

The driver section may maintain the current lens position of the imaging section 200 when the selection result of the lens position selection section 350 has changed within a given time after the lens position selection section 350 has selected the near point-side lens position LN in a state in which the far point-side lens position LF is selected, or has selected the far point-side lens position LF in a state in which the near point-side lens position LN is selected.

According to the above configuration, since the lens position does not change at least for the given time, it is possible to further suppress a frequent change in the in-focus object plane position. For example, since it is difficult to maintain the object and the imaging section 200 of the endoscope apparatus at a constant distance due to the motion of an internal organ and the like, a situation may occur in which the imaging section 200 approaches the object for just a moment, and the original distance is then recovered. According to the above configuration, since the lens position does not change when the imaging section 200 has approached the object for just a moment, it is possible to prevent an unnecessary change in the in-focus object plane position.

The phase difference calculation section 330 may calculate the phase difference at a rate lower than a frame rate at which the imaging section 200 acquires the captured image (described later with reference to FIGS. 12 to 15). The lens position selection section 350 may select the lens position of the imaging section 200 based on the phase difference calculated at a rate lower than the frame rate.

According to the above configuration, since the lens position does not change after calculating the phase difference until the phase difference is subsequently calculated, it is possible to suppress a frequent change in the in-focus object plane position.

3. Second Embodiment 3.1. Focus Lens Driver Section

A second embodiment of the invention is described below. An endoscope apparatus according to the second embodiment is basically configured in the same manner as the endoscope apparatus according to the first embodiment (see FIG. 1). Description of a configuration and an operation similar to those described above in connection with the first embodiment is appropriately omitted.

The operation of the focus lens driver section 230 is described below with reference to FIG. 9. The focus lens driver section 230 moves the focus lens 220 to the discrete lens position LN or LF to change the in-focus object plane position to the in-focus object plane position NEAR or FAR (see FIG. 9). The depth of field DN (di to dk2) at the in-focus object plane position NEAR and the depth of field DN (dk1 to dj) at the in-focus object plane position FAR overlap with each other within the range of dk1 to dk2 (i.e., the distance to the object). Specifically, the object is brought into focus when the distance to the object is within the range of dk1 to dk2 irrespective of whether the in-focus object plane position is changed to the in-focus object plane position NEAR or FAR.

3.2. AF Control Method

An AF control method according to the second embodiment is described below.

A look-up table (see FIG. 10) in which the phase difference and the distance to the object are linked is provided in advance. The lens position selection section 350 acquires the distance corresponding to the phase difference calculated by the phase difference calculation section 330 from the look-up table to calculate the distance to the object from the imaging section.

The near point-side lens position LN and the far point-side lens position LF (see FIG. 9) are set in advance. As illustrated in FIG. 10, the position of the focus lens at which the object is brought into focus when the distance to the object is within the range of di to dk2 (di<dk2) (depth of field DN) is set to be the lens position LN. The position of the focus lens at which the object is brought into focus when the distance to the object is within the range of dk1 to dj (dk1<dj) (depth of field DF) is set to be the lens position LF.

It is possible to provide an image in which the object is brought into focus when the distance to the object is within the range of di to dj by appropriately changing the lens position to the lens position LN or the lens position LF. In other words, two positions to which the focus lens is moved are set to the lens position LN and the lens position LF when it is desired to provide an image in which the object is brought into focus when the distance to the object is within the range of di to dj.

The boundary position setting section 340 sets a first boundary position dk1 and a second boundary position dk2 in advance based on the information about the depth of field. As illustrated in FIG. 9, the first boundary position dk1 corresponds to the near point-side edge of the depth of field DF, and the second boundary position dk2 corresponds to the far point-side edge of the depth of field DN. Note that the boundary position setting section 340 may set the boundary positions dk1 and dk2 based on a boundary position that has been set via the external I/F section 380.

The lens position selection section 350 compares the distance to the object that corresponds to the phase difference with the boundary position dk2 set by the boundary position setting section 340 when the current position of the focus lens 220 is the near point-side lens position LN. The lens position selection section 350 maintains the near point-side lens position LN when the distance to the object is equal to or shorter than the boundary position dk2. The lens position selection section 350 selects the far point-side lens position LF when the distance to the object is longer than the boundary position dk2.

The lens position selection section 350 compares the distance to the object that corresponds to the phase difference with the boundary position dk1 set by the boundary position setting section 340 when the current position of the focus lens 220 is the far point-side lens position LF. The lens position selection section 350 maintains the far point-side lens position LF when the distance to the object is equal to or longer than the boundary position dk1. The lens position selection section 350 selects the near point-side lens position LN when the distance to the object is shorter than the boundary position dk1.

The distance to the object may frequently change across the boundary position when the distance to the object is close to the boundary position since the object or the endoscope apparatus may move forward and backward, for example. When only one boundary position is provided, the lens position frequently changes to the lens position LN or the lens position LF when the distance to the object frequently changes across the boundary position. Since the zoom magnification differs between the lens position LN and the lens position LF, it is difficult for the user to observe the object due to a change in the zoom magnification.

According to the second embodiment, the near point-side lens position LN is selected when the distance to the object is equal to or shorter than the boundary position dk1, the far point-side lens position LF is selected when the distance to the object is equal to or longer than the boundary position dk2, and the current in-focus object plane position is maintained when the distance to the object is within the range of dk1 to dk2. According to the above configuration, since the current in-focus object plane position is maintained even if the distance to the object is close to the boundary position, the lens position is not frequently changed between the lens position LN and the lens position LF, and the user can observe the object at a constant zoom magnification.

3.3. Second AF Control Method

An AF control method that directly utilizes the phase difference is described below.

Figure 11:
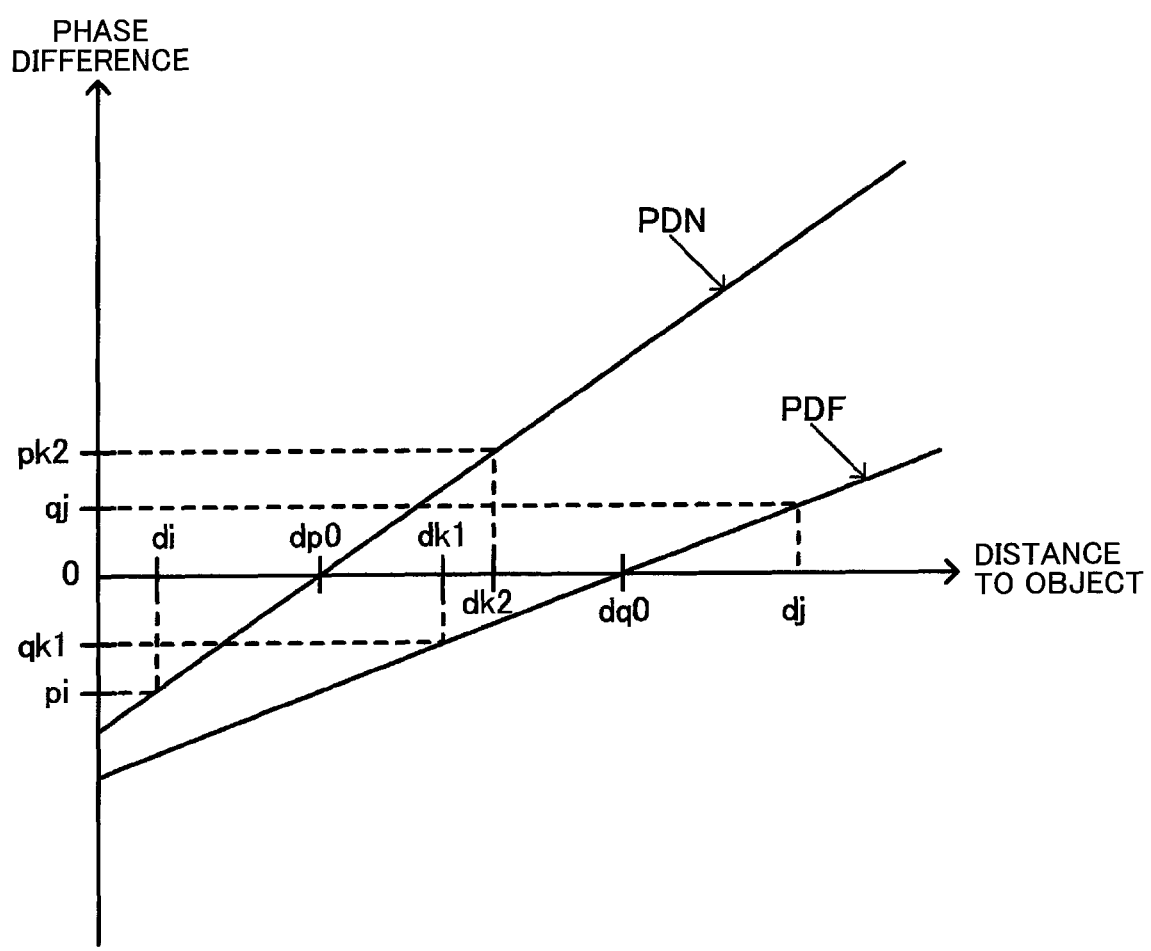
FIG. 11 illustrates an example of phase difference characteristics according to the second embodiment.

FIG. 11 illustrates an example of the phase difference characteristics with respect to the distance to the object. Note that PDN is the phase difference characteristics when the focus lens is set to the near point-side lens position LN, and PDF is the phase difference characteristics when the focus lens is set to the far point-side lens position LF. The phase difference pk2 (corresponding to the first phase difference pk in FIG. 3) corresponds to the boundary position dk2 (see the phase difference characteristics PDN), and the phase difference qk1 (corresponding to the second phase difference qk in FIG. 3) corresponds to the boundary position dk1 (see the phase difference characteristics PDF).

The lens position selection section 350 compares the phase difference calculated by the phase difference calculation section 330 with the phase differences pk2 and qk1 that correspond to the boundary position, and selects (changes) the lens position. Specifically, the lens position selection section 350 maintains the focus lens 220 at the near point-side lens position LN when the phase difference calculated by the phase difference calculation section 330 is equal to or smaller than the phase difference pk2 in a state in which the near point-side lens position LN (phase difference characteristics PDN) is selected, and selects the far point-side lens position LF when the phase difference calculated by the phase difference calculation section 330 is larger than the phase difference pk2 in a state in which the near point-side lens position LN is selected. The lens position selection section 350 maintains the focus lens 220 at the far point-side lens position LF when the phase difference calculated by the phase difference calculation section 330 is equal to or larger than the phase difference qk1 in a state in which the far point-side lens position LF (phase difference characteristics PDF) is selected, and selects the near point-side lens position LN when the phase difference calculated by the phase difference calculation section 330 is smaller than the phase difference qk1 in a state in which the far point-side lens position LF is selected.

Figure 9:
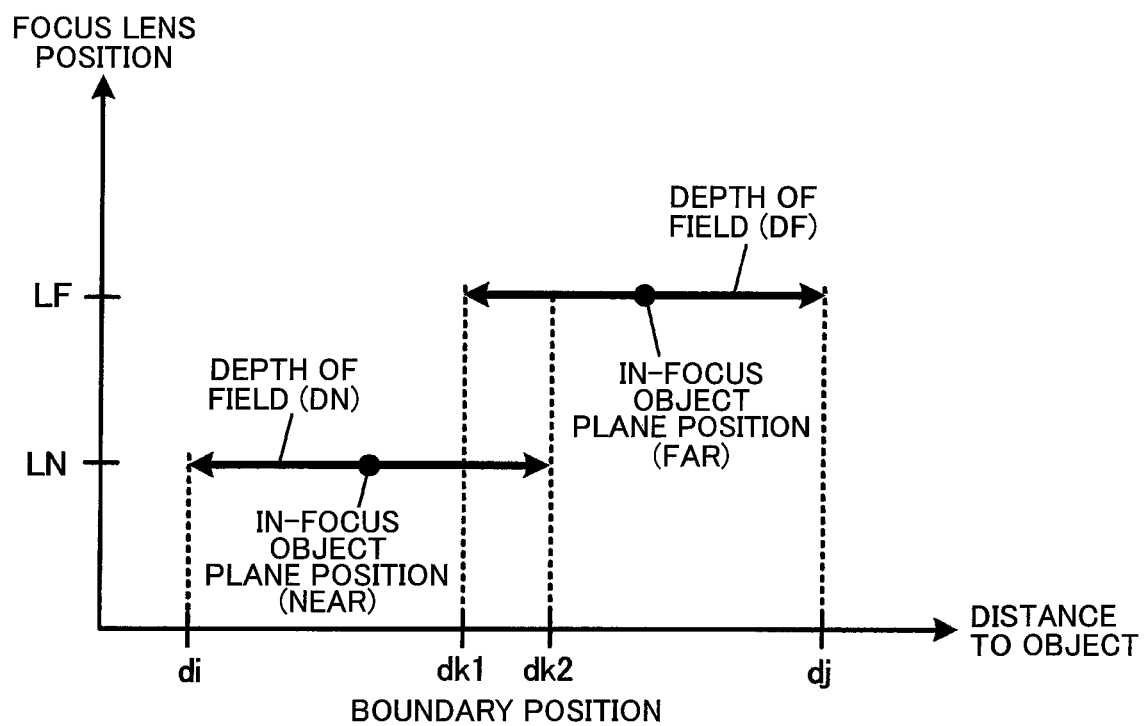
FIG. 9 is a view illustrating the operation of a focus lens driver section according to a second embodiment.

According to the second embodiment, the boundary position setting section 340 sets the first boundary position dk1 and the second boundary position dk2 between the near point-side in-focus object plane position NEAR that corresponds to the near point-side lens position LN and the far point-side in-focus object plane position FAR that corresponds to the far point-side lens position LF, the second boundary position dk2 being farther from the imaging section 200 than the first boundary position dk1 (see FIG. 9 and the like). The lens position selection section 350 selects the near point-side lens position LN when the lens position selection section 350 has determined that the position of the object corresponding to the phase difference is closer to the imaging section 200 than the first boundary position dk1, selects the far point-side lens position LF when the lens position selection section 350 has determined that the position of the object corresponding to the phase difference is farther from the imaging section 200 than the second boundary position dk2, and maintains the currently selected lens position when the lens position selection section 350 has determined that the position of the object corresponding to the phase difference is situated between the first boundary position dk1 and the second boundary position dk2.

According to the above configuration, since the lens position does not change when the object lies between the first boundary position dk1 and the second boundary position dk2, it is possible to suppress a frequent change in the in-focus object plane position even when the object lies close to the boundary position.

The boundary position setting section 340 may set the first boundary position dk1 at the near point-side edge of the depth of field DF when the far point-side lens position LF is selected, and may set the second boundary position dk2 at the far point-side edge of the depth of field DN when the near point-side lens position LN is selected (see FIG. 9 and the like).

According to the above configuration, since the depth of field DN and the depth of field DF overlap each other, the object can be reliably brought into focus even in the vicinity of the boundary between the depth of field DN and the depth of field DR It is also possible to determine whether or not the object lies outside the current depth of field by setting the first boundary position dk1 at the near point-side edge of the depth of field DF and setting the second boundary position dk2 at the far point-side edge of the depth of field DN, and select an appropriate lens position at which the object is brought into focus.

4. Phase Detection AF Method

The image sensor 240 that is provided with the phase difference detection element for implementing phase detection AF, and a phase detection AF method that utilizes the image sensor 240 are described below. Note that the phase detection AF method is not limited to the method described below. For example, various other phase detection AF methods (e.g., a method that implements pupil division using a spectacle lens) may also be employed.

FIG. 12 illustrates a configuration example of an image sensor that is provided with a phase difference detection element. The image sensor illustrated in FIG. 12 includes normal pixels R, G, and B having a Bayer color filter array, and phase difference sensors S1 and S2 (pixels S1 and S2) (phase difference detection elements).

The pixels S1 and S2 (phase difference sensors S1 and S2) are the functional pixels S1 and S2 disclosed in paragraphs [0074] to [0083] of JP-A-2000-156823, for example. Each of the pixels S1 and S2 (phase difference sensors S1 and S2) has an opening that is biased from the center of the pixel in the lateral direction. The above configuration achieves an effect similar to that achieved when dividing the pupil of the imaging optical system in the lateral direction. Therefore, image signals from a plurality of phase difference sensors S1 and S2 arranged in the horizontal direction in FIG. 12 can be considered to be the phase signals of a light beam that has passed through each pupil. For example, when the position of the object image formed by the imaging optical system coincides with the image plane of the image sensor (i.e., the object is in focus), the phase signals output from the phase difference sensors S1 coincide with the phase signals output from the phase difference sensors S2. When the position of the object image formed by the imaging optical system is situated in front of (or behind) the image plane of the image sensor (i.e., the object is out of focus), a phase difference occurs between the phase signals output from the phase difference sensors S1 and the phase signals output from the phase difference sensors S2. Note that only a pair of phase difference sensors S1 and S2 may be provided at the center of the imaging section, or a plurality of pairs of phase difference sensors S1 and S2 may be provided at arbitrary positions of the imaging section, for example.

The phase difference calculation section 330 calculates the moving amount of the movable lens as described below (see FIG. 13). The movable lens is the focus lens 220 illustrated in FIG. 1. Note that the movable lens may be the zoom lens when implementing a magnification adjustment and a focus adjustment by driving only the zoom lens, or may be the focus lens when independently adjusting the zoom lens and the focus lens.

Figure 13:
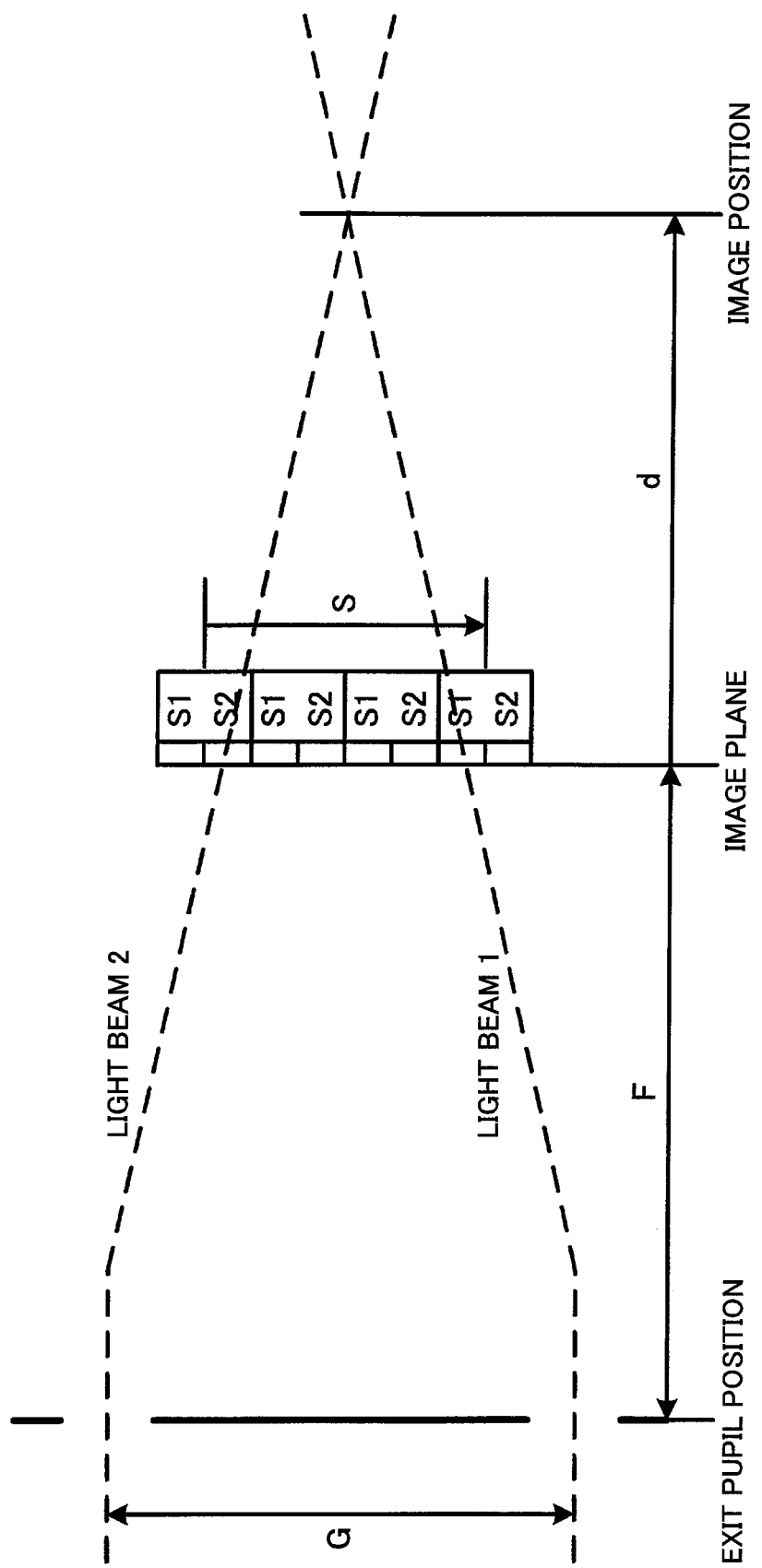
FIG. 13 is a view illustrating the operation of a phase detection AF process.

FIG. 13 is a view illustrating light beams that pass through divided pupils when the image position is situated behind the image plane. The light beam 1 is a light beam that has passed through the pupil corresponding to each phase difference sensor S1, and the light beam 2 is a light beam that has passed through the pupil corresponding to each phase difference sensor S2. Since the image position is situated at a position differing from the image plane (i.e., a position behind the image plane), a phase difference S occurs between the phase signals output from the phase difference sensors S1 and the phase signals output from the phase difference sensors S2. Note that S is a positive or negative vector. The direction indicated by the arrow in FIG. 13 is the positive direction. The phase difference S may be calculated using a known phase detection AF technique. The phase difference calculation section 330 calculates the phase difference S from the phase signals sequentially output from the phase difference sensors S1 and S2 in the same cycle as the image signals, for example, and sequentially outputs the calculated phase difference S to the lens position selection section 350.

Note that the phase difference calculation section 330 may calculate the defocus amount or the in-focus lens position as the phase difference information, and output the defocus amount or the in-focus lens position to the lens position selection section 350. Specifically, the distance between the image plane and the exit pupil is referred to as F, the distance between the centers of gravity of the divided pupils is referred to as G, and the defocus amount is referred to as d. Note that d is a positive or negative vector. The direction indicated by the arrow in FIG. 13 is the positive direction. In this case, the following expression (2) is satisfied. The defocus amount d can be calculated using the following expression (3) obtained by transforming the expression (2). Note that the above description similarly applies to the case where the image position is situated in front of the image plane. The defocus amount d may also be calculated by the method disclosed in paragraphs [0108] to [0110] of JP-A-2000-156823, for example.

$$G/(F+d)=S/d \quad (2)$$

$$d=F \cdot S/(G-S) \quad (3)$$

The phase difference calculation section 330 calculates the moving amount of the movable lens necessary for implementing an in-focus state from the defocus amount d calculated using the expression (3) for the phase signals sequentially output from the phase difference sensors S1 and S2 in the same cycle as the image signals, for example, and sequentially outputs the calculated moving amount to the lens position selection section 350. Alternatively, the phase difference calculation section 330 may calculate the in-focus lens position from the moving amount of the movable lens and information about the current position of the movable lens, and sequentially output information about the calculated in-focus lens position to the lens position selection section 350. For example, the ratio Rt of the moving amount of the movable lens to the moving amount of the image position may be calculated in advance by the following expression (4) using the design data of the imaging optical system, and the moving amount D may be calculated by the following expression (5).

$$Rt=\text{moving amount of movable lens/moving amount of image position} \quad (4)$$

$$D=-Rt \cdot d \quad (5)$$

When the phase difference calculation section 330 calculates the defocus amount d or the in-focus lens position, the lens position selection section 350 selects the lens position LN or the lens position LF based on the defocus amount d or the in-focus lens position. Since the defocus amount d or the in-focus lens position is a value linked to the phase difference S, the AF control process can be performed using a method similar to the method described with reference to FIGS. 4B, 5B, and 11.

For example, when the ratio Rt of the moving amount of the movable lens to the moving amount of the image position changes depending on the position x of the movable lens, the position xn (n is a natural number) of the movable lens and the ratio Rn may be stored as in advance as a look-up table (LUT) (see FIG. 14), and the ratio Rn corresponding to the position xn of the movable lens at a timing at which the phase signals have been output from the phase difference sensors S1 and S2 may be used as the ratio Rt in the expression (5) to calculate the moving amount D.

When the distance F between the image plane and the exit pupil and the distance G between the centers of gravity of the pupils (see FIG. 13) also change depending on the position x of the movable lens, the distance Fn and the distance Gn corresponding to the position xn of the movable lens are also stored in the LUT (see FIG. 15). The distance Fn and the distance Gn corresponding to the position xn of the movable lens at a timing at which the phase signals have been output from the phase difference sensors S1 and S2 are used as the distance F and the distance G in the expression (3) to calculate the defocus amount dn. The calculated defocus amount dn and the ratio Rn corresponding to the position xn of the movable lens are used as the defocus amount d and the ratio Rt in the expression (5) to calculate the moving amount D. Note that it is unnecessary to take account of the parameter illustrated in FIG. 15 of which the change depending on the position of the movable lens is negligibly small. Another parameter that may be used to calculate the moving amount and changes to a large extent depending on the position of the movable lens may be added to the LUT.

The phase difference calculation section 330 may calculate and output the moving amount corresponding to all of the phase signals sequentially output from the phase difference sensors S1 and S2, or may sample the phase signals in an arbitrary cycle, and calculate and output the moving amount, for example. In the latter case, the moving amount is output from the phase difference calculation section 330 in a cycle longer than the image signal output cycle.

Although only some embodiments of the present invention have been described in detail above, those skilled in the art will readily appreciate that many modifications are possible in the embodiments without materially departing from the novel teachings and advantages of this invention. Accordingly, all such modifications are intended to be included within scope of this invention.

What is claimed is:

1. An endoscope apparatus comprising:
    an imaging section that includes a phase difference detection element for implementing phase detection autofocus, and acquires a captured image by imaging an object;
    a phase difference calculation section that calculates a phase difference based on a signal output from the phase difference detection element;
    a lens position selection section that selects a lens position that is either a near point-side lens position or a far point-side lens position based on the phase difference, the near point-side lens position and the far point-side lens position being discrete lens positions set in advance;
    a driver section that changes a lens position of the imaging section to the lens position selected by the lens position selection section; and
    a control section that outputs a control signal to control an intensity of illumination light that is applied to the object,
    wherein the lens position selection section determines whether or not the intensity is smaller than a given threshold value based on the control signal when the phase difference calculation section cannot calculate the phase difference, selects the near point-side lens position when the lens position selection section has determined that the intensity is smaller than the threshold value, and selects the far point-side lens position when the lens position selection section has determined that the intensity is larger than the threshold value.

2. The endoscope apparatus as defined in claim 1, further comprising:
    a boundary position setting section that sets a boundary position between a near point-side in-focus object plane position that corresponds to the near point-side lens position and a far point-side in-focus object plane position that corresponds to the far point-side lens position,
    wherein the lens position selection section selects the near point-side lens position when the lens position selection section has determined that a position of an object corresponding to the phase difference is closer to the imaging section than the boundary position, and selects the far point-side lens position when the lens position selection section has determined that the position of the object corresponding to the phase difference is farther from the imaging section than the boundary position.

3. The endoscope apparatus as defined in claim 2, wherein the boundary position setting section sets the boundary position at a boundary between a depth of field when the near point-side lens position is selected and a depth of field when the far point-side lens position is selected.

4. The endoscope apparatus as defined in claim 2, wherein the lens position selection section stores a look-up table that indicates a relationship between the phase difference and a distance to the object from the imaging section when the near point-side lens position is selected, and a relationship between the phase difference and a distance to the object from the imaging section when the far point-side lens position is selected, and
    wherein the lens position selection section acquires a distance that corresponds to the phase difference calculated by the phase difference calculation section from the look-up table, and selects the lens position of the imaging section based on the acquired distance.

5. The endoscope apparatus as defined in claim 2, wherein the lens position selection section stores a first phase difference corresponding to the boundary position when the near point-side lens position is selected, and a second phase difference corresponding to the boundary position when the far point-side lens position is selected, and
    wherein the lens position selection section selects the far point-side lens position when the lens position selection section has determined that the phase difference calculated by the phase difference calculation section is larger than the first phase difference in a state in which the near point-side lens position is selected, and selects the near point-side lens position when the lens position selection section has determined that the phase difference calculated by the phase difference calculation section is smaller than the second phase difference in a state in which the far point-side lens position is selected.

6. The endoscope apparatus as defined in claim 1, wherein the driver section maintains a current lens position of the imaging section for a given time after changing the lens position of the imaging section from the near point-side lens position to the far point-side lens position, or after changing the lens position of the imaging section from the far point-side lens position to the near point-side lens position.

7. The endoscope apparatus as defined in claim 1, wherein the driver section maintains a current lens position of the imaging section when a selection result of the lens position selection section has changed within a given time after the lens position selection section has selected the near point-side lens position in a state in which the far point-side lens position is selected, or has selected the far point-side lens position in a state in which the near point-side lens position is selected.

8. The endoscope apparatus as defined in claim 1, wherein the phase difference calculation section calculates the phase difference at a rate lower than a frame rate at which the imaging section acquires the captured image, and wherein the lens position selection section selects the lens position of the imaging section based on the phase difference calculated at a rate lower than the frame rate.

9. The endoscope apparatus as defined in claim 8, wherein the imaging section includes an image sensor that includes the phase difference detection element in its pixel array, and wherein the imaging section acquires the signal output from the phase difference detection element when capturing the captured image using the image sensor.

10. The endoscope apparatus as defined in claim 1, wherein the control section controls the intensity such that a brightness of the captured image stays constant.

* * * * *